(12) United States Patent
Videira et al.

(10) Patent No.: US 11,353,460 B2
(45) Date of Patent: Jun. 7, 2022

(54) L2A5 ANTIBODY OR FUNCTIONAL FRAGMENT THEREOF AGAINST TUMOUR ANTIGENS

(71) Applicants: UNIVERSIDADE NOVA DE LISBOA, Lisbon (PT); INSTITUTO PORTUGUÊS DE ONCOLOGIA DO PORTO FG, EPE, Oporto (PT); HELMHOLTZ-ZENTRUM DRESDEN-ROSSENDORF—INSTITUTE OF RADIOPHARMACEUTICAL CANCER RESEARCH, Dresden (DE)

(72) Inventors: Paula Alexandra Quintela Videira, Caparica (PT); Carlos Manuel Mendes Novo, Caparica (PT); Liliana Raquel Rodrigues Loureiro, Caparica (PT); Mylène Adelaide do Rosário Carrascal, Caparica (PT); José Alexandre Ribeiro de Castro Ferreira, Caparica (PT); Maria Angelina de Sá Palma, Caparica (PT); Lúcio Lara Santos, Caparica (PT); Luís Carlos Oliveira Lima, Caparica (PT); Wengang Chai, Caparica (PT); Michael Bachmann, Caparica (PT)

(73) Assignees: UNIVERSIDADE NOVA DE LISBOA, Lisbon (PT); INSTITUTO PORTUGUÊS DE ONCOLOGIA DO PORTO FG, EPE, Oporto (PT); HELMHOLTZ-ZENTRUM DRESDEN-ROSSENDORF—INSTITUTE OF RADIOPHARMACEUTICAL CANCER RESEARCH, Dresden (DE)

( * ) Notice: Subject to any disclaimer, the term of this patent is extended or adjusted under 35 U.S.C. 154(b) by 130 days.

(21) Appl. No.: 16/964,900

(22) PCT Filed: Jan. 17, 2019

(86) PCT No.: PCT/PT2019/000001
§ 371 (c)(1),
(2) Date: Jul. 24, 2020

(87) PCT Pub. No.: WO2019/147152
PCT Pub. Date: Aug. 1, 2019

(65) Prior Publication Data
US 2021/0033616 A1 Feb. 4, 2021

(30) Foreign Application Priority Data
Jan. 26, 2018 (PT) .......................................... 110526

(51) Int. Cl.
*G01N 33/574* (2006.01)
*A61P 35/00* (2006.01)
*C07K 16/30* (2006.01)

(52) U.S. Cl.
CPC ........ *G01N 33/57492* (2013.01); *A61P 35/00* (2018.01); *C07K 16/3076* (2013.01); *C07K 16/3092* (2013.01); *C07K 2317/41* (2013.01); *C07K 2317/565* (2013.01)

(58) Field of Classification Search
None
See application file for complete search history.

(56) References Cited

FOREIGN PATENT DOCUMENTS

| WO | 2016057916 A1 | 4/2016 | |
|---|---|---|---|
| WO | 2017040529 A1 | 3/2017 | |
| WO | WO-2018217116 A1 * | 11/2018 | ....... G01N 33/57492 |

OTHER PUBLICATIONS

Loureiro et al 2015 (Challenges in Antibody Development against Tn and Sialyl-Tn antigens, Biomolecules, vol. 5, 2015) (Year: 2015).*
Loureiro et al (Third CRI-CIMT-EATI-AACR International Cancer Immunotherapy Conference, Sep. 6-9, 2017; Poster Session, Abstract A094, p. 78) (Year: 2017).*
Loureiro, L.R. et al., "Novel monoclonal antibody L2A5 specifically targeting sialyl-Tn and short glycans terminated by alpha-2-6 sialic acids," Scientific Reports, vol. 8, No. 1, pp. 1-16, Aug. 15, 2018.
Loureiro, L. et al., Challenges in Antibody Development against Tn and Sialyl-Tn Antigens, Biomolecules, vol. 5, No. 3, pp. 1783-1809, Aug. 11, 2015.
Loureiro, L.R. et al., "Development of a novel target module redirecting UniCAR T cells to Sialyl Tn-expressing tumor cells," Blood Cancer Journal, vol. 8, No. 9, pp. 1-6, Aug. 22, 2018.
International Search Report and Written Opinion dated Mar. 18, 2019 in International Patent Application No. PCT/PT2019/000001.

* cited by examiner

*Primary Examiner* — Laura B Goddard
*Assistant Examiner* — Sarah A Alsomairy
(74) *Attorney, Agent, or Firm* — Patrick J. Halloran

(57) ABSTRACT

This invention provides an antibody or functional antibody fragments, or probe thereof directed against a unique group of antigens identified in cancer.
The present invention comprises nucleotide sequences derived from L2A5 monoclonal antibody. The antibody or functional antibody fragment, or probe thereof includes a variable heavy chain domain and a variable light chain domain that has an amino acid sequence provided herein. This DNA/amino acid sequence conjugation is unique and has never been described before. The present invention further provides antibody or functional antibody fragment or a conjugate or a recombinant protein useful in the detection, treatment and prevention of human disease, including cancer.

21 Claims, 9 Drawing Sheets
Specification includes a Sequence Listing.

Sialyl Tn:
    NeuAcα2-6GalNAcα1- (sialyl Tn)

2,6-sialyl T:
        Galβ1-3GalNAcα1-
                  |
      NeuAcα2-6 disialyl T:
NeuAcα2-3Galβ1-3GalNAcα1-
                      |
        NeuAcα2-6

2,6-sialolactosamine:
NeuAcα2-6Galβ1-4Glcβ1

SEQUENCE LISTING

```
<160> NUMBER OF SEQ ID NOS: 25

<210> SEQ ID NO 1
<211> LENGTH: 339
<212> TYPE: DNA
<213> ORGANISM: Mus musculus

<400> SEQUENCE: 1
gaagtgcagc tgcaggagtc cggacctggc ctcgtgaaac cttctcagtc tctgtctctc      60
acctgctctg tcattggcta ctccatcacc agtggttatt actggaactg gatccggcag     120
tttccaggaa acaaactgga atggatgggc tccataaact acgacggtag caatatctac     180
aatccatctc tcaaagatcg aatctccatc actcgtgaca catctaagaa ccagtttttc     240
ctgaagttga attctgtgac tactgaggac acagctacat attactgtgc aagaggggggg    300 gactactggg gtcaaggaac ctcagtcacc gtctcctca                            339

<210> SEQ ID NO 2
<211> LENGTH: 351
<212> TYPE: DNA
<213> ORGANISM: Mus musculus

<400> SEQUENCE: 2
gatattgtgc tgacccagac tccagcaatc atgtctgcat ctccagggga gaaggtcacc      60
ttgacctgca gtgccagctc aagtgtaagt tacatgcact ggttccagca aaagtcaggc     120
acctccccca aaagatggat ttatgacaca tccaaactgg cttctggagt ccctgctcgc     180
ttcagtggca gtgggtctgg gacctcttac tctctcacaa tcagcagcat ggaggctgag     240
gatgctgccg cttattactg ccagcagtgg agtagtgacc cacccatgct cacgttcggt     300
gctgggacca agctggagct gaaacgggct gatgctgcac caactgtatc c               351

<210> SEQ ID NO 3
<211> LENGTH: 113
<212> TYPE: PRT
<213> ORGANISM: Mus musculus

<400> SEQUENCE: 3

Glu Val Gln Leu Gln Glu Ser Gly Pro Gly Leu Val Lys Pro Ser Gln
1               5                   10                  15

Ser Leu Ser Leu Thr Cys Ser Val Ile Gly Tyr Ser Ile Thr Ser Gly
                20                  25                  30

Tyr Tyr Trp Asn Trp Ile Arg Gln Phe Pro Gly Asn Lys Leu Glu Trp
            35                  40                  45

Met Gly Ser Ile Asn Tyr Asp Gly Ser Asn Ile Tyr Asn Pro Ser Leu
```

```
                50                  55                  60
Lys Asp Arg Ile Ser Ile Thr Arg Asp Thr Ser Lys Asn Gln Phe Phe
 65                  70                  75                  80

Leu Lys Leu Asn Ser Val Thr Glu Asp Thr Ala Thr Tyr Tyr Cys
                 85                  90                  95

Ala Arg Gly Gly Asp Tyr Trp Gly Gln Gly Thr Ser Val Thr Val Ser
            100                 105                 110

Ser

<210> SEQ ID NO 4
<211> LENGTH: 107
<212> TYPE: PRT
<213> ORGANISM: Mus musculus

<400> SEQUENCE: 4

Ile Val Leu Thr Gln Thr Pro Ala Ile Met Ser Ala Ser Pro Gly Glu
  1               5                  10                  15

Lys Val Thr Leu Thr Cys Ser Ala Ser Ser Val Ser Tyr Met His
                 20                  25                  30

Trp Phe Gln Gln Lys Ser Gly Thr Ser Pro Lys Arg Trp Ile Tyr Asp
             35                  40                  45

Thr Ser Lys Leu Ala Ser Gly Val Pro Ala Arg Phe Ser Gly Ser Gly
         50                  55                  60

Ser Gly Thr Ser Tyr Ser Leu Thr Ile Ser Ser Met Glu Ala Glu Asp
 65                  70                  75                  80

Ala Ala Ala Tyr Tyr Cys Gln Gln Trp Ser Ser Asp Pro Pro Met Leu
                 85                  90                  95

Thr Phe Gly Ala Gly Thr Lys Leu Glu Leu Lys
            100                 105

<210> SEQ ID NO 5
<211> LENGTH: 25
<212> TYPE: PRT
<213> ORGANISM: Mus musculus

<400> SEQUENCE: 5

Ile Val Leu Thr Gln Thr Pro Ala Ile Met Ser Ala Ser Pro Gly Glu
  1               5                  10                  15

Lys Val Thr Leu Thr Cys Ser Ala Ser
                 20                  25

<210> SEQ ID NO 6
<211> LENGTH: 5
<212> TYPE: PRT
<213> ORGANISM: Mus musculus

<400> SEQUENCE: 6

Ser Ser Val Ser Tyr
  1               5

<210> SEQ ID NO 7
<211> LENGTH: 17
<212> TYPE: PRT
<213> ORGANISM: Mus musculus

<400> SEQUENCE: 7

Met His Trp Phe Gln Gln Lys Ser Gly Thr Ser Pro Lys Arg Trp Ile
  1               5                  10                  15

Tyr
```

<210> SEQ ID NO 8
<211> LENGTH: 3
<212> TYPE: PRT
<213> ORGANISM: Mus musculus

<400> SEQUENCE: 8

Asp Thr Ser
1

<210> SEQ ID NO 9
<211> LENGTH: 36
<212> TYPE: PRT
<213> ORGANISM: Mus musculus

<400> SEQUENCE: 9

Lys Leu Ala Ser Gly Val Pro Ala Arg Phe Ser Gly Ser Gly Ser Gly
1               5                   10                  15

Thr Ser Tyr Ser Leu Thr Ile Ser Ser Met Glu Ala Glu Asp Ala Ala
            20                  25                  30

Ala Tyr Tyr Cys
        35

<210> SEQ ID NO 10
<211> LENGTH: 11
<212> TYPE: PRT
<213> ORGANISM: Mus musculus

<400> SEQUENCE: 10

Gln Gln Trp Ser Ser Asp Pro Pro Met Leu Thr
1               5                   10

<210> SEQ ID NO 11
<211> LENGTH: 25
<212> TYPE: PRT
<213> ORGANISM: Mus musculus

<400> SEQUENCE: 11

Glu Val Gln Leu Gln Glu Ser Gly Pro Gly Leu Val Lys Pro Ser Gln
1               5                   10                  15

Ser Leu Ser Leu Thr Cys Ser Val Ile
            20                  25

<210> SEQ ID NO 12
<211> LENGTH: 9
<212> TYPE: PRT
<213> ORGANISM: Mus musculus

<400> SEQUENCE: 12

Gly Tyr Ser Ile Thr Ser Gly Tyr Tyr
1               5

<210> SEQ ID NO 13
<211> LENGTH: 17
<212> TYPE: PRT
<213> ORGANISM: Mus musculus

<400> SEQUENCE: 13

Trp Asn Trp Ile Arg Gln Phe Pro Gly Asn Lys Leu Glu Trp Met Gly
1               5                   10                  15

Ser

```
<210> SEQ ID NO 14
<211> LENGTH: 7
<212> TYPE: PRT
<213> ORGANISM: Mus musculus

<400> SEQUENCE: 14

Ile Asn Tyr Asp Gly Ser Asn
1               5

<210> SEQ ID NO 15
<211> LENGTH: 38
<212> TYPE: PRT
<213> ORGANISM: Mus musculus

<400> SEQUENCE: 15

Ile Tyr Asn Pro Ser Leu Lys Asp Arg Ile Ser Ile Thr Arg Asp Thr
1               5                  10                  15

Ser Lys Asn Gln Phe Phe Leu Lys Leu Asn Ser Val Thr Thr Glu Asp
            20                  25                  30

Thr Ala Thr Tyr Tyr Cys
        35

<210> SEQ ID NO 16
<211> LENGTH: 6
<212> TYPE: PRT
<213> ORGANISM: Mus musculus

<400> SEQUENCE: 16

Ala Arg Gly Gly Asp Tyr
1               5

<210> SEQ ID NO 17
<211> LENGTH: 15
<212> TYPE: DNA
<213> ORGANISM: Mus musculus

<400> SEQUENCE: 17
tgaagtgtaa gttac                                              15

<210> SEQ ID NO 18
<211> LENGTH: 33
<212> TYPE: DNA
<213> ORGANISM: Mus musculus

<400> SEQUENCE: 18
cagcagtgga gtagtgaccc acccatgctc acg                          33

<210> SEQ ID NO 19
<211> LENGTH: 27
<212> TYPE: DNA
<213> ORGANISM: Mus musculus

<400> SEQUENCE: 19
ggctactcca tcaccastgg ttattac                                 27

<210> SEQ ID NO 20
<211> LENGTH: 21
<212> TYPE: DNA
<213> ORGANISM: Mus musculus

<400> SEQUENCE: 20
ataaactacg acggtagcaa t                                       21
```

```
<210> SEQ ID NO 21
<211> LENGTH: 18
<212> TYPE: DNA
<213> ORGANISM: Mus musculus

<400> SEQUENCE: 21
gcaagagggg gggactac                                                     18

<210> SEQ ID NO 22
<211> LENGTH: 33
<212> TYPE: DNA
<213> ORGANISM: Mus musculus
<220> FEATURE:
<221> NAME/KEY: misc_feature
<222> LOCATION: (16)..(16)
<223> OTHER INFORMATION: n is a, c, g, or t

<400> SEQUENCE: 22
tttttggatc csartnmagc tgsagsagtc wgg                                    33

<210> SEQ ID NO 23
<211> LENGTH: 30
<212> TYPE: DNA
<213> ORGANISM: Mus musculus

<400> SEQUENCE: 23
attgggacta gtttctgcga cagctggatt                                        30

<210> SEQ ID NO 24
<211> LENGTH: 36
<212> TYPE: DNA
<213> ORGANISM: Mus musculus

<400> SEQUENCE: 24
tttttgaatt ctgayattgt gmtsacmcar wctmca                                 36

<210> SEQ ID NO 25
<211> LENGTH: 32
<212> TYPE: DNA
<213> ORGANISM: Mus musculus

<400> SEQUENCE: 25
tttttgggcc cggatacagt tggtgcagca tc                                     32
```

L2A5 ANTIBODY OR FUNCTIONAL FRAGMENT THEREOF AGAINST TUMOUR ANTIGENS

CROSS-REFERENCE TO RELATED APPLICATIONS

This application is a U.S. National Stage entry application of International Application No. PCT/PT2019/000001, filed Jan. 17, 2019 and claims the benefit of priority to Portuguese Application No. 110526, filed Jan. 26, 2018.

REFERENCE TO SEQUENCE LISTING SUBMITTED ELECTRONICALLY The instant application contains a Sequence Listing which has been submitted electronically in ASCII format and is hereby incorporated by reference in its entirety. Said ASCII copy, created on Jan. 26, 2018, is named SEQUENCELISTING.txt and is 5,871 bytes in size.

TECHNICAL FIELD

The present invention provides an antibody or functional antibody fragments, or probe thereof directed against a group of antigens identified in cancer.

STATE OF THE ART

The sialyl Tn (STn) is a short O-glycan antigen, a disaccharide consisting of sialic acid linked to N-acetyl galactosamine, i.e. Neu5Acα-2,6GalNAc, which is in turn O-linked to serine or threonine residues in a polypeptide chain, in an alpha configuration trough the GalNAc residue. Its relevance has to do with the fact of being absent in normal healthy tissues but detected at various frequencies in almost all kind of carcinomas (Julien, Videira, & Delannoy, 2012). In addition, STn is a target for metastatic, drug resistant and high malignant cancer cells. Their motivating characteristics include:

1) association of STn expression with oncogenesis and metastatic ability of human cancer cells, and cancer initiating cells (Okasaki et al., 2012).

2) correlation of STn with a poor prognosis in patients, with reduced overall survival and lack of response to chemotherapy (Choi et al., 2000) and 3) evasion from immune protection (Carrascal et al., 2014).

Alpha-2,6 sialic acids are typically terminating cancer biomarkers. Short alpha 2,6 sialylated O-glycans are overexpressed in several types of cancer. They are generally involved in cancer progression and metastasis. In addition, they may contribute to immune evasion through their recognition by a number of immune receptors such as the sialic acid binding proteins (Siglecs) (Crocker, Paulson, & Varki, 2007; Nicoll et al., 2003).

Thus, the present invention provides an antibody, functional antibody fragments or probes that bind specifically cancer biomarkers. Besides the specific identification of tumour cells, these antibodies have the potential to block the recognition of such ligands by host cell receptors, involved in the mechanism underlying tumour progression, including immune tolerance.

There are relevant numbers of antibodies that have been approved to treat cancer patients (https://www.cancer.org/). They comprise:

1. Monoclonal antibodies (mAb) that target cancer specific (associated) antigens. The recombinant humanized mAb anti-HER2 trastuzumab (Herceptin™) is described in various scientific publications, for example Cancer Res., 1998, 58: 2825-2831. It, targets the HER2 receptors expressed in nearly 30% of breast cancer patients. The patent WO0105425 describes an anti-tumour composition comprising an alkylating anthracycline coupled to the anti-HER2 trastuzumab antibody. However, these treatments are only available for a limited number of patients (30% of breast cancer patients). Also, the HER2 proteins that is targeted by the trastuzumab antibody is also expressed in relevant normal cells, such as cardiac cells, this accounting for the associated cardiotoxicity. The present invention allows developing recombinant antibodies that target a wider list of receptors beyond the HER2, expressed by different types of cancer, that are decorated with STn or a group of glycans terminated by alpha-2,6 sialic acids. This will potentially allow the development of therapies for a wider group of cancer patients. Since both STn and glycans terminated by alpha-2,6 sialic acids are highly overexpressed by cancer cells, it also has the potential of greater specificity and reduced toxicity.

2. MAbs that block molecules that stop the immune system working. They are called immune checkpoint inhibitors and include drugs that block CTLA-4, PD-1 and PD-L1. Examples of PD-1 inhibitors are Pembrolizumab (Keytruda) and Nivolumab (Opdivo) which are approved to treat melanoma of the skin, non-small cell lung cancer, kidney cancer, bladder cancer, head and neck cancers, and Hodgkin lymphoma. The immune checkpoints however do not provide an immediate anti-tumour response and are typically used as adjuvant therapy. Also, immune checkpoint inhibitors can allow the immune system to attack some normal organs in the body, which can lead to serious side effects in some people.

3. MAbs that block cell signalling necessary for cancer cells to divide. These include the Bevacizumab (Avastin®) that targets VEGF that affects blood vessel growth and the Cetuximab (Erbitux®), an antibody that targets a cell protein called EGFR, which is important for cell growth. However, these antibodies, that block cell signalling, also influence physiologic mechanisms, and are associated with toxicity, such as high blood pressure, bleeding, blood clots, and kidney damage.

There are some patent documents (EP 2014302 WO 2015053871 A4; U.S. Pat. No. 7,423,126 B2; EP 2993184 A1) that claim the nucleic acids encoding human antibodies to tumour associated carbohydrate antigens; however, none the antibodies within above-mentioned patent documents recognize STn antigen, which is the target of the present invention antibody.

The patent application EP2680004 (A2) claims the antibodies against sialylated glycans, including STn antigen that contains N-acetylneuraminic acid (NeuAc) or N-glycolylneuraminic acid (NeuGc), whereas the present invention regards of an antibody that is specific for STn antigen mainly with NeuAc and a group of glycans terminated by alpha-2,6 sialic acids.

The patent applications WO 1998046246 A1 and WO 1995029927 A3 claim methods to produce α-O-linked glycoconjugates or glycosides of tumour-associated carbohydrate antigens, which include the 2,6 sialyl T antigen. While mentioning the possibility of being used to develop antibodies for treating cancer, none of these patent applications provide an antibody sequence to detect the 2,6-sialyl T antigen, nor the group of related 2,6-sialic acid-containing antigens that are subject of the present patent.

Several patent applications have claimed antibodies that bind sialic acid residues, such as CA 2743032 A1, which characterize an IgM antibody that recognize sialic acid residues, including NeuGc, or US 20160184450 A1 and U.S.

Pat. No. 8,148,335 B2 that claim antibodies that specifically binds a de-N-acetylated sialic acid, or EP 2302390 A1 and US 20120142903 A1 patent applications that includes antibodies recognizing NeuGc structure; whereas, the present invention claims an antibody that recognize not only NeuAc bound to GalNAc (STn antigen) but also the structure of NeuAc within a group of glycans terminated by alpha-2,6-linked sialic acids.

The EP 2261255 A1 patent application described the production of antibodies in chicken recognizing the monosaccharide NeuAc and the US 20110034676 A1 patent application claims the production. and purification of polyclonal antibodies against both Neu5Ac and Neu5Gc structures. Yet, the present invention claims nucleic acids encoding mAbs produced in mouse that target the oligosaccharides STn antigen and a group of glycans terminated by alpha-2,6-linked sialic acids. This is an advantage, as the present invention will allow distinguishing tumour associated glycans, and not just the monosaccharide NeuAc, which is also expressed in normal cells.

Furthermore, US 2010/0034825 A1 patent application the production of antibodies against MUC1 glycoprotein, using immunization with long Tn- or STn-MUC1 tandem repeat glycopeptides. This work differs from the present invention, as the target structure is different, i.e. targets MUC1 glycoprotein, and not glycan structures, STn nor glycans terminated by alpha-2,6-linked sialic acids.

The WO2016057916A1 patent antibodies recognize STn antigen and not the glycans terminated by alpha-2,6-linked sialic acids.

According to the above mentioned, tumour antigens are often not tumour-specific due to its concurrent expression in normal cells. Therefore, target therapies typically show associated toxicity due to off target effects. Tumour antigens are not pan-tumour antigens and are confined to specific types or grades of cancers. Therefore, target therapies are typically confined to specific subsets of cancers.

Consequently, there is a need to develop antibodies or functional antibody fragments, or probes thereof directed against a unique group of antigens only identified in cancer cells.

A unique nucleic acid sequence that allows producing an antibody or functional antibody fragments or probe thereof to target sialylated glycans such as STn, 2,6-sialyl T, disialyl T and 2,6-sialo-N-acetyllactosamine, which are overexpressed in different types and subtypes of cancer cells is very important.

The present invention relates with nucleotide sequences encoding mAbs against the STn and a group of glycans terminated by alpha-2,6-linked sialic acids. These antigens are short-chain glycans that are overexpressed in cancer but not expressed by normal cells. These antigens are also ligands for immune receptors and dampen the activity of the immune system against tumour cells, thus can also be considered ligands for immune checkpoints.

DESCRIPTION

Monoclonal antibody (mAbs) refers to an antibody that is produced by a single B cell clone. MAbs can be also produced by an hybridoma, which is a hybrid between a B cell and myeloma cell, or cell lines that express recombinant DNA coding for the immunoglobulin heavy and light chain, and therefore will produce a single and specific antibody.

The antibodies are expressed to the extracellular milieu and then purified from there.

The specificity of an antibody is its ability to react with one antigen or a group of antigens that share a certain epitope. An epitope, also known as antigenic determinant, is the part of an antigen that is recognized by the antibody.

An antibody belongs to the immunoglobulin class of proteins and it is an assembling of two identical heavy chains (~50-70 kDa) and two identical light chains (~25 kDa). In the amino-terminal of each heavy or light chain there is a sequence of 100-130 amino acids that code the variable region. In the carboxyl-terminal of each heavy or light chain there is a sequence that codes the constant region. Each antibody binds twice the same antigen, i.e. is bivalent.

The antigen-binding fragment (Fab) is the antibody fragment that binds to antigens. Each Fab is composed of one constant and one variable domain from each heavy and light chain of the antibody. The Fragment crystallisable (Fc) region is composed of 2 or 3 domains of the carboxy-terminal of the two heavy chains. While the Fab ensures binding to the antigen, the Fc region ensures that each antibody generates an effector immune response. The Fc region binds to various cell receptors, such as Fc receptors, and other molecules, such as complement proteins, mediating different physiological effects including opsonisation to facilitate phagocytosis by phagocytes, cell lysis by Natural killer cells, and degranulation of mast cells, basophils and eosinophils.

The term "variable domain" or "variable region" is the amino-terminal part of the light or heavy chains of an antibody that interacts with the antigen. It has a length of about 120 to 130 amino acids in the heavy chain and about 100 to 110 amino acids in the light chain. The sequences of each of the variable regions are substantially varied, particularly in the complementary determining regions (CDRs), responsible for the interaction with the specific antigen. The CDRs are flanked by less varied framework regions (FR). The CDRs of each of the light and heavy chains are three. The CDRs L1, L2, and L3 are within the light chain. The CDRs H1, H2 and H3 are within the heavy chain.

The expression "functional antibody fragment or probe" is a part of the antibody that includes the variable region of the heavy and the light chain of the antibody, or includes either the variable region of the heavy or the variable region of the light chain of the antibody. The functional antibody fragment or probe retains most or all the binding activity of the initial antibody from which the fragment or probe was derived. Such functional antibody fragments or probes can include the single chain Fv (scFv), diabody, triabody, tetrabody and minibody.

The term "nucleotide sequences" refers to a sequence of nucleotides of any length, either deoxy ribonucleotides or ribonucleotides or analogues thereof.

The nucleotide sequence can be transcribed to produce mRNA, which is then translated into a polypeptide and/or a fragment thereof.

The potential treatment derived from the present invention refers to the use in the treatment, management or amelioration of a disease associated with expression of STn or a group of alpha-2,6 sialylated glycans. In the present embodiments, a possible treatment refers to an antibody, functional antibody fragment or probe derived from the invention, in its native or modified form.

A possible treatment can also be included in the present invention in combination with an agent which is well known to be useful for, or has been or is currently being used for the treatment, management or amelioration of a disease.

The potential use as diagnostic agent refers to a substance that when administered into a subject will help in the diagnosis of a disease. Such substances can be used to detect and/or define the localization of a disease of a process that derives from the progression of the disease. It also includes a substance that can help to predict response to a certain treatment or the prognostic of a disease. In certain embodiments, the use of a diagnostic agent implies the conjugation of the antibody or functional antibody fragment or probe of the present invention with a reporter molecule, such as fluorescence, enzyme, or secondary antibody.

The sialyl Tn, a.k.a, STn, sialosyl Tn, sialylated Tn, Neu5Ac-α2,6GalNAcα-O-Ser/Thr or also referred to as CD175s by the "cluster of differentiation" nomenclature is the simplest sialylated mucin-type O-glycan. The STn is a truncated O-glycan containing a sialic acid (Neu5Ac) α-2,6 linked (via carbon 6) to N-acetyl-galactosamine (GalNAc) alpha-O-linked to a Serine/Threonine (Ser/Thr) (Neu5Ac-α2,6GalNAcα-O-Ser/Thr). The sialylation prevents the formation of various core structures otherwise found in mucin-type O-glycans.

STn is associated with an adverse outcome and poor prognosis in cancer patients. The biosynthesis of the STn antigen has been linked to the expression of the sialyltransferase ST6GalNAc1, and to mutations or loss of heterozygosity of the COSMC gene.

STn is expressed by more than 80% of human carcinomas and is linked to poor prognosis in cancer patients.

The invention provides nucleotide sequences encoding an antibody heavy or light chain or a functional antibody fragment or a probe thereof, wherein the antibody heavy or light chain or functional antibody fragment or probe thereof encoded by the nucleotide sequence of the invention has one or more of the CDRs listed in Tables 1 and 2. An antibody or functional antibody fragment or probe thereof that includes one or more of the CDRs can specifically bind to STn or a group of alpha-2,6 sialylated glycans. Specifically binding includes the specificity, affinity and/or avidity as provided in Example I.

In another aspect, an antibody or functional fragment thereof encoded by the polynucleotides of the invention can include the complement dependent cytotoxicity activity and/or antibody-dependent cell-mediated cytotoxicity (ADCC) activity.

The method for the production of the antibody of the invention can include fusion between two cells producing an hybridoma, introducing a nucleotide sequence of the invention into a host cell, culturing the host cell under conditions and for a sufficient time to produce the encoded heavy and/or light chain of an antibody or functional fragment of the invention, and purifying the heavy and/or light chain of an antibody or functional fragment.

Recombinant expression of an antibody or functional antibody fragment or probe thereof of the invention that binds to STn or a group of alpha-2,6 sialylated antigens can include construction of an expression vector containing a nucleotide sequence that encodes the heavy and/or light chain of an antibody or functional antibody fragment or probe thereof of the invention.

The vector can be produced by recombinant DNA technology. Such vectors can also include other coding nucleotide sequences, originating a chimeric sequence. For instance, can include the nucleotide sequence encoding the constant region of the antibody molecule (WO 86/05807 and WO 89/01036) enabling the expression of a chimera protein containing the amino acid sequence of the antibody, functional antibody fragment or probe thereof of the present invention followed by the entire heavy, or and light chain, or both the entire heavy and light chains.

The expression vector can be transferred to a host cell by Transfection/Transduction techniques and the resulting cells produce the antibody or functional fragment thereof of the invention. Thus, the invention includes host cells containing nucleotide sequences encoding the antibody or functional antibody fragment or probe thereof of the invention.

The host cell can be chosen to modify the characteristics of the product derived from the inserted nucleotide sequences.

In an embodiment, these host cells can add glycosylation or phosphorylation sites or other modifications to the coded proteins. In another embodiment, the host cells can provide the correct processing and cell trafficking/secretion of the proteins.

A single-chain fragment variable antibody (scFv) refers to a functional antibody fragment containing only the VL and VH regions, which are joined via a linker, forming a monovalent antigen binding site. Diabodies, tribodies and tetrabodies are antibodies including dimers, trimers or tetramers of scFv, i.e. containing two, three and four polypeptide chains, respectively, and forming two, three and four antigen binding sites, respectively, which can be the same or different.

The resulting antibody, functional antibody fragments or probes thereof of this invention can have one or more binding sites. If containing more than one binding site, these sites can be identical to one another or can be different. In case of two different binding sites, the antibody, functional antibody fragment or probe is named a "bispecific" antibody.

Site-directed and PCR-mediated mutagenesis which results in amino acid substitutions can be used to introduce mutations in the CDR regions that improve affinity, while preserving the specificity of the antibody of the invention.

In some embodiments, the antibody, functional antibody fragment or probe of the invention is conjugated or fused to one or more diagnostic agent, or therapeutic agent or any other desired molecule. The resulting conjugated antibody, functional antibody fragment or probe can be useful for monitoring or diagnosing the onset, development, progression and/or severity of a disease associated with the expression of STn or alpha-2,6 sialylated glycans.

As example, but not limited to, the antibody may be conjugated to a therapeutic agent to induce cell killing or other effect. A therapeutic agent can be a chemotherapeutic drug; a taxan; an antimetabolite, an alkylating agent, an antibiotic, an antimitotic agent, a hormone, a nucleoside analogue, a kinase inhibitor, a radioactive metal ion, a toxin, a cytokine, or an antiangiogenic agent.

The antibody or functional fragment of the invention can also be used to detect the expression of STn or alpha-2,6 sialylated glycans in any biological sample using classical immunohistological methods or immunoassays, such as the enzyme linked immunosorbent assay (ELISA) and the radio-immunoassay (RIA), flow cytometry, and immunoblotting.

The antibody, functional antibody fragment or probe thereof of the invention can be included alone or conjugated or in combination in a pharmaceutical composition, provided in an effective concentration, to wield a therapeutically useful effect, with minimal side effects.

SUMMARY OF THE INVENTION

The present invention provides an antibody, functional antibody fragments or probes thereof that specifically bind sialyl Tn (STn) and a group of glycans terminated by alpha 2,6-linked sialic acids.

The antibody, functional antibody fragment or probes thereof binds to the antigen binding site. An example of nucleotide sequences code for the variable heavy and light chains, are SEQ ID Nos. 1 and 2, respectively.

The antibody was obtained after mice immunisation with mucins containing sialyl Tn (STn). Nucleotide sequences were derived from the L2A5 monoclonal antibody. One nucleotide sequence provides the variable heavy (VH) chain (SEQ ID No. 1) and comprises the H-CDR1. (GGCTACTC-CATCACCASTGGTTATTAC (SEQ ID No. 19). amino acid SEQ ID No. 12), H-CDR2 (ATAAAC-TACGACGGTAGCAAT (SEQ ID No. 20), amino acid SEQ ID No. 14), and H-CDR3 (GCAAGAGGGGGGGACTAC (SEQ ID No. 21), amino acid SEQ ID No. 16), One nucleotide sequence; provides a variable light (VL) chain (SEQ ID No. 3) which comprises the complementary determining regions (CDR): L-CDR1 (TGAAGTGTAAGTTAC (SEQ ID No. 17). amino acid SEQ ID No. 6), L-CDR2 (GACACATCC, amino acid SEQ ID No. 8), and L-CDR3 (CAGCAGTGGAGTAGTGACCCACCCATGCTCACG (SEQ ID No. 18), amino acid SEQ ID No. 10).

The combination of the L-CDR1, L-CDR2, and L-CDR3 of the light chain and the H-CDR1, H-CDR2, and H-CDR3 of the heavy chain generate unique sequences that code for peptide sequences which recognize not only the disaccharide STn antigen, but unexpectedly, it also recognizes a group of glycans terminated by alpha-2,6 sialic acids also overexpressed in cancer. These peptide sequences are used to generate further antibodies, functional antibody fragments or probes. This overall group of glycans recognized by the antibodies, functional antibody fragments or probes comprises the Sialyl Tn:

2,6-sialyl T:

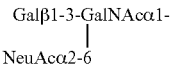

disialyl T:

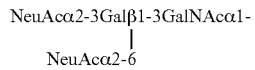

2,6-sialo-N-acetyllactosamine:

Antibodies with such specificity are particularly interesting because of their high tumour specificity and low or absent reactivity to normal cells, contrary to current antibodies and antibody-based anticancer therapies.

The isolated polynucleotide of the invention can also include a nucleic acid sequence provided herein, wherein the nucleic acid sequence encodes the variable heavy and light chain domain of the antibody, functional antibody fragments or probes. Examples of the nucleic acid sequence are SEQ ID Nos. 1 and 2, respectively.

In another aspect, the present invention provides an antibody, functional antibody fragments or probes thereof that specifically bind STn and a group of glycans terminated by alpha 2,6-linked sialic acids for use in a method of detecting a tumour in a subject.

In some embodiments, the invention provides pharmaceutical compositions comprising the antibody, functional antibody fragments or probes of the invention and a pharmaceutically acceptable carrier.

In another embodiment, the invention provides pharmaceutical compositions comprising the antibody, functional antibody fragments or probes that block cell-cell or receptor-ligand interactions.

In some embodiments, the invention provides a method for treating or preventing a disease in a subject in need, by administering a therapeutically effective amount of a pharmaceutical composition of the invention.

Without intent to limit the disclosure herein, this disclosure presents attached drawings of illustrated embodiments for an easier understanding.

DESCRIPTION OF THE DRAWINGS

FIG. 7 shows the glycan antigen sequences bound by the L2A5 antibody. Glycan specificity was determined by means of glycan microarray analysis.

FIG. 8 shows that using UniCAR T cells armed with TMs specific for the STn antigen kills tumours cells. Statistical analysis was performed using one-way ANOVA with Bonferroni multiple-comparison test (**$p<0.01$).

DETAILED DESCRIPTION OF THE INVENTION

Figure 1:
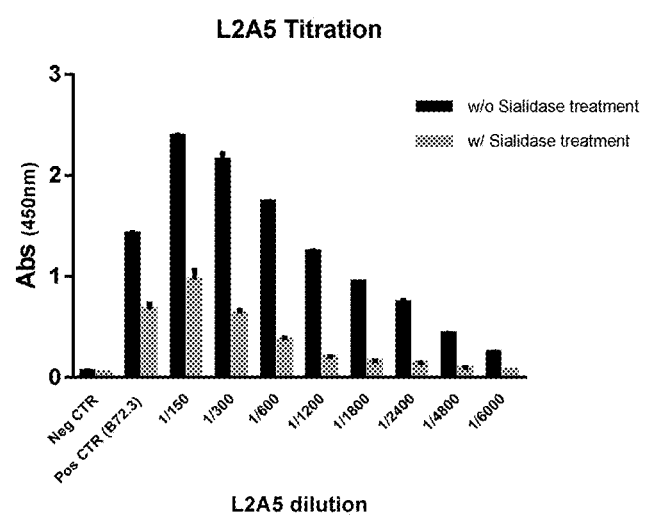
FIG. 1 shows the titre and binding of the L2A5 antibody to animal mucins using indirect ELISA. Antibody titration was performed using various coating concentrations of bovine submaxillary mucins (BSM) previously treated or not with sialidase. Phosphate buffer was used as negative control and binding of anti-STn antibody B72.3 to BSM as positive control. Binding of L2A5 mAb was detected with goat anti-mouse IgG-conjugated to horseradish peroxidase.

The present invention provides an antibody, functional antibody fragments or probes thereof that specifically bind STn and a group of glycans terminated by alpha 2,6-linked sialic acids.

The antibody, functional antibody fragment or probes thereof binds to the antigen binding site. An example of nucleotide sequences code for the variable heavy and light chains, are SEQ ID Nos. 1 and 2, respectively.

The isolated polynucleotide of the invention can also include a nucleic acid sequence provided herein, wherein the nucleic acid sequence encodes the variable heavy and light chain domain of the antibody, functional antibody fragments or probes.

The present invention further provides compositions to produce an antibody, functional antibody fragments or probes thereof that specifically bind STn and a group of glycans terminated by alpha 2,6-linked sialic acids.

The compositions include nucleotide sequences encoding the antigen binding site of an antibody, a functional antibody fragment or probes. The compositions include nucleotide sequences that code for the variable heavy and light chains.

The isolated polynucleotide of the invention can also include a nucleic acid sequence provided herein, wherein the nucleic acid sequence encodes the variable heavy and light chain domain of the antibody, functional antibody fragments or probes.

In another aspect, the present invention provides an antibody, functional antibody fragments or probes thereof that specifically bind STn and a group of glycans terminated by alpha 2,6-linked sialic acids for use in a method of detecting a tumour in a subject.

In some embodiments, the invention provides pharmaceutical compositions comprising the nucleotide sequences encoding the antibody, functional antibody fragments or probes of the invention and a pharmaceutically acceptable carrier.

In another embodiment, the invention provides pharmaceutical compositions comprising the nucleotide sequences encoding the antibody, functional antibody fragments or probes that block cell-cell or receptor-ligand interactions.

In some embodiments, the invention provides a method for treating or preventing a disease in a subject in need, by administering a therapeutically effective amount of a pharmaceutical composition of the invention.

The method comprises the following steps:
a) Staining a biological sample obtained from a subject possibly having a tumour with an antibody that specifically binds STn and a group of glycans terminated by alpha 2,6-linked sialic acids, in which the mentioned staining is made under conditions suitable for specific binding of the antibody, or functional antibody fragments or probes thereof to the STn, 2,6-sialyl T, disialyl T or 2,6-sialolactosamine;
b) And wherein the presence or the absence of the binding of the antibody is indicative of the presence or the absence of tumour cells expressing cell surface STn, 2,6-sialyl T, disialyl T or 2,6-sialolactosamine.

Biological sample, as used herein, comprises isolated cells, or tissue, or tumour derived proteins.

Sialylated glycans are over-expressed in several types of cancer cells compared to the matching healthy cells, where its expression was negligible. The highest STn frequencies is found in pancreas, colorectal and ovarian cancers, where almost 100% of the cancer cells express STn (Julien et al 2012). Frequency in bladder cancers is 75% (Ferreira et al 205). Lung adenocarcinoma expresses nearly 80% and cervical cancer, cholangiocarcinoma, oesophagus, colon and breast cancer have frequencies between 50 and 70%. In addition, STn over-expression occurs earlier in carcinogenesis and the loss of cell differentiation, which often participates in a high histological grade classification, positively modulates the STn expression (Julien et al).

Sialylated glycans can be targetable by antibodies, functional antibody fragments or probes with high affinity and specificity. The present invention further provides compositions for producing antibodies, functional antibody fragments or probes that bind STn and a group of glycans terminated by alpha-2,6 sialic acids.

These compositions were obtained by immunization of 6 weeks old female Balb/c mice with ovine serum mucins, using methods such as those described in example I.

Mice serum showing reactivity for STn-positive cell lines, STn-positive mucins or cell lysates were selected, by means of the methods, such as those described in examples II or III or VI. Splenocytes from those immunized mice showing serum with reactivity for STn, were harvested and fused with a myeloma cell (Sp2/0) to obtain an immortalized hybridoma cell expressing antibodies.

Methods for hybridoma technique, such as the one described in example IV are well described in the art.

Hybridoma supernatants were screened for the presence of antibodies against STn by methods, such as those described in examples II or III or VI. Selected hybridomas were expanded for antibody production and characterization. From the several anti-STn mAbs obtained, mAb L2A5 was selected as lead candidate and used for further analysis. Reactivity against mucin proteins with a heavy content of STn and the antibody titre of L2A5 mAb was determined by using methods as described in example II and represented in FIG. 1. In addition, desialylation by means of the sialidase treatment was performed to assess recognition of sialylated structures by L2A5 antibody. As shown in FIG. 1, the reactivity of the L2A5 mAb increases with the mAb concentrations in a logarithmic manner. A high immunoreactivity to BSM was observed, reaching the endpoint titre of 6 000. Furthermore, treatment with sialidase clearly demonstrated a reduction of reactivity of this antibody to BSM, showing the specific and dependent binding to sialylated structures. Noteworthy, in similar methods to those described in example II, but where the mucin proteins bearing STn were replaced by desialylated (asialo) mucins, the L2A5 antibody displayed no reactivity.

Sialylated glycans are overexpressed in cancer cells and can be targetable by antibodies, functional antibody fragments or probes with high affinity and specificity.

The present invention provides compositions for producing an antibody, functional antibody fragments or probes thereof that bind STn and a group of glycans terminated by alpha-2,6 sialic acids.

Glycosylation is critical for the quality and development of therapeutic mAbs. Glycosylation patterns change with selected expression system or culture conditions with a significant impact on its pharmacokinetics and pharmacodynamics. The control of glycosylation is therefore essential to ensure the safety and efficacy of the molecules. For therapeutic cancer cell targeting, antibody-dependent cell-mediated cytotoxicity (ADCC), complement-dependent cytotoxicity (CDC), antibody dependent cell-mediated phagocytosis (ADCP) and direct cell apoptosis are critical for efficacies.

MAbs produced in murine myeloma cell line SP2/0 can add sugars that are not naturally found on normal human IgG with impact in terms of immunogenicity.

In an embodiment of the present invention, changes in glycan composition of IgG molecule is done at the glycosylation sites Asn88 and Asn297 through the manipulation of the mannose, sialic acids, fucose and galactose residues in order to increase the efficacy of the therapeutic antibody (review in Liming Liu 2015).

In one embodiment, non-human antibodies can be humanized, which refers to the construction of chimeric immunoglobulins, that contain the amino acid sequence of interest derived from the original non-human antibody (e.g. the mouse antibody) included in a human immunoglobulin (recipient antibody). In the humanized antibodies, the CDR amino acid residues of the human antibody are replaced by residues from the CDRs of a non-human species (e.g. the mouse antibody) having the desired specificity, affinity and capacity. In general, humanized antibodies will comprise at least one, and typically two, variable domains, in which all or almost all of the CDR regions correspond to those of a non-human antibody and all or part of the FR regions are those of a human immunoglobulin.

In one embodiment, immune cells such as the T cells are modified to express the antibody (all or part) or receptors that bind an antibody, i.e. a chimeric antigen receptors (CAR). CARs are molecules that combine antibody specificity for a desired antigen (e.g., tumor antigen) with a T cell receptor-activating intracellular domain to generate a chimeric receptor that exhibits a specific anti-tumour cellular immune activity. In one embodiment, the antigen recognition domain of these modified T cells binds to a tumour associated antigen. In one embodiment, it relates to the adoptive cell transfer of T cells modified to express a CAR.

CAR can be produced using a variety of techniques known in the art, including but not limited to the use of RNA-guided endonucleases, in particular Cas9/CRISPR system, to specifically engineered T cells to express CARs (WO 2014191128 A1). In another embodiment, a target module composed of a binding moiety specific for a certain human cell surface protein and a tag, wherein the tag is derived from any human nuclear protein, preferably from human nuclear La protein is used (WO2016030414 A1).

Also, the antibody or functional fragment of the invention could be linked to nanoparticles, insert in liposomes membrane in order to be used as specific vector to delivery in situ toxic compounds inducing apoptosis as well metal ions useful for hyperthermia therapy.

The compositions for producing an antibody, functional antibody fragments or probes thereof of the present invention were obtained by immunization of 6 weeks old female Balb/c mice with ovine serum mucins, using methods such as those described in example I. Mice serum showing reactivity for STn-positive cell lines, STn-positive mucins or cell lysates were selected, by means of the methods, such as those described in examples II or III or VI. Splenocytes from those immunized mice showing serum with reactivity for STn, were harvested and fused with a myeloma cell in order to obtain an immortalized hybridoma cell expressing anti-STn antibodies. Methods for hybridoma technique, such as the one described in example IV are well described in the art. Hybridoma supernatants were screened for the presence of antibodies against STn by methods, such as those described in examples II or III or VI. Selected hybridomas were expanded for antibody production and characterization. From the several anti-STn mAbs obtained, mAb L2A5 was selected as lead candidate and used for further analysis. Reactivity against mucin proteins with a heavy content of STn and the antibody titre of L2A5 mAb was determined by using methods as described in example II and represented in FIG. 1. In addition, desialylation by means of the sialidase treatment was performed to assess recognition of sialylated structures by L2A5 antibody. As shown in FIG. 1, the reactivity of the L2A5 mAb increases with the mAb concentrations in a logarithmic manner.

A high immunoreactivity to BSM was observed, reaching the endpoint titre of 6 000. Furthermore, treatment with sialidase clearly demonstrated a reduction of reactivity of this antibody to BSM, showing the specific and dependent binding to sialylated structures. Noteworthy, in similar methods to those described in example II, but where the mucin proteins bearing STn were replaced by desialylated (asialo) mucins, the L2A5 antibody displayed no reactivity.

Figure 2:
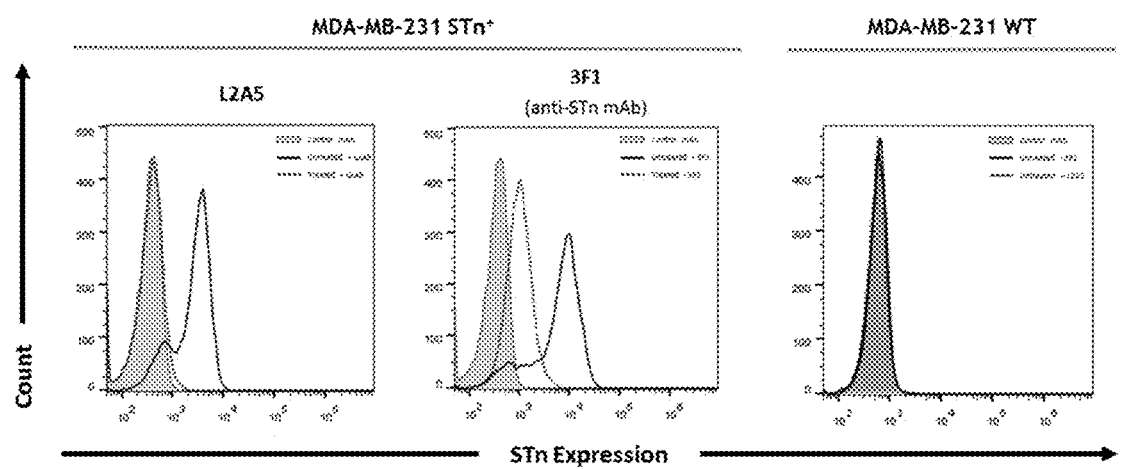
FIG. 2 shows the binding of the L2A5 to the cell surface of tumour cells. The binding of the L2A5 antibody was assessed by flow cytometry and using cancer cells lines transduced or not (wild type) with the ST6GalNAc1 gene and thus overexpress the STn antigen. The figure shows representative histogram of relative cell count L2A5 antibody in STn positive and WT breast cancer cell line MDA-MB-231. 3F1 antibodies (anti-STn antibodies) were used or the secondary anti-mouse Ig-FITC antibody (grey profile). To assess binding specificity to sialylated antigens, the STn-expressing cell lines were desialylated by sialidase treatment. Solid and dashed lines represent the histograms for sialidase untreated and treated cell, respectively. X-axis represents fluorescence, related to STn expression.

Binding of L2A5 mAb to viable MDA-MB-231 cancer cells was confirmed by using methods as described in example III. As a model, it was used MDA-MB-231 cancer cells that express the STn antigen, due to the overexpression of the gene ST6GalNAc1. As shown in FIG. 2, the L2A5 mAb shows a high reactivity to 80 to 88% of STn$^+$ cells. The reactivity was considerably decreased after treatment of the cancer cell lines with sialidase. As also shown in FIG. 2, the L2A5 presented no binding to wild type MDA-MB-231 cancer cells, which do not express the STn antigen. Taken together, these results confirmed the specificity and selectivity of L2A5 mAb against the STn antigen presented on a cancer cell surface. As also represented in FIG. 2, other anti-STn antibodies, that also react with STn, show slight distinct binding profiles, in relation to the cancer cell line MDA-MB-231.

Figure 3:
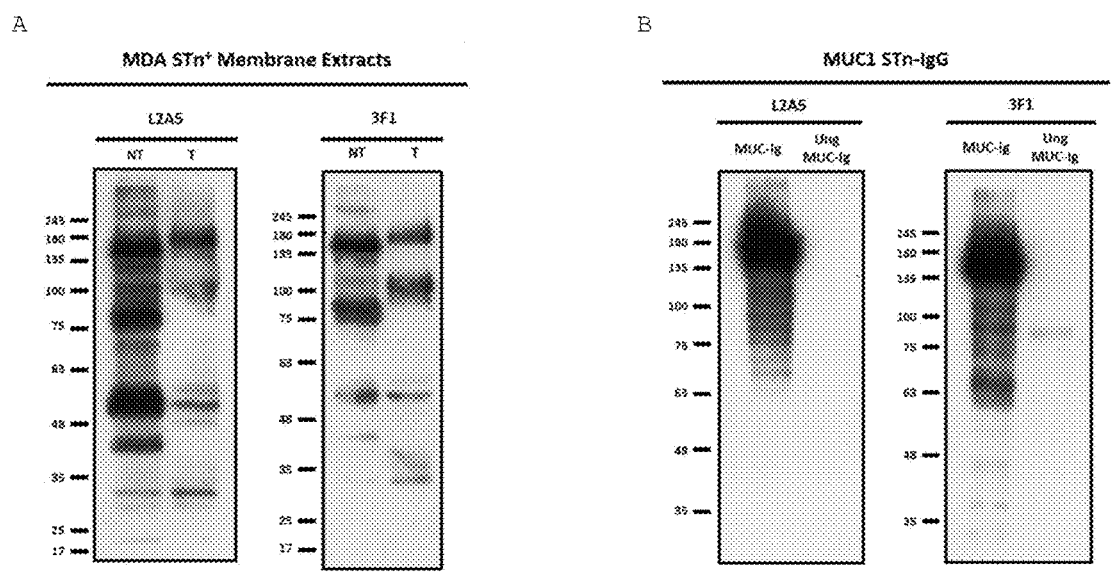
FIG. 3 shows the reactivity of the L2A5 antibody to membrane bound proteins and to recombinant human Mucin 1 (MUC1). Western blot analysis of anti-STn antibodies 3F1 and L2A5 binding to membrane extracts of STn-expressing MDA-MB-231 cell line and to chimeric protein of MUC1 heavily decorated with STn plus the human Ig Fc region. MDA-MB-231 STn+ membrane extracts (A) and chimeric protein MUC1 STn-IgG (B) were stained with 3F1 and L2A5 antibodies. In addition to blotting of untreated membrane extracts and chimeric protein (NT), membrane extracts samples were desialylation using sialidase (T) or unglycosylated MUC1 STn-IgG protein were used (Ung).

To confirm binding specificity of L2A5 mAb to STn bearing membrane proteins, assays as those described in example VI were performed. As shown in FIG. 3, the L2A5 mAb reacted with proteins derived from the MDA-MB-231 cell line that overexpresses the ST6GalNAc1, and therefore the STn. The profile showed reactiveness to proteins with the molecular weights above 245 kDa and approximately 160, 85, 50 and 40 kDa. Upon desialylation of the membrane proteins, it is observed a decrease or abolishment of the reactivity, confirming the binding of the L2A5 mAb to sialylated proteins. Membrane proteins derived from the wild type cancer cells, which do not express the STn antigen, did not provide positive reactivity with the L2A5 mAb. As shown also in FIG. 3, L2A5 demonstrated a robust binding to MUC1 STn-IgG (approximately 180 kDa) but not to no glycosylated MUC1 STn-IgG. Taken together, the results indicate that L2A5 mAb recognizes STn-antigen in membrane extracts of STn expressing cancer cells as well as on STn carrier proteins such as MUC1.

Figure 4:
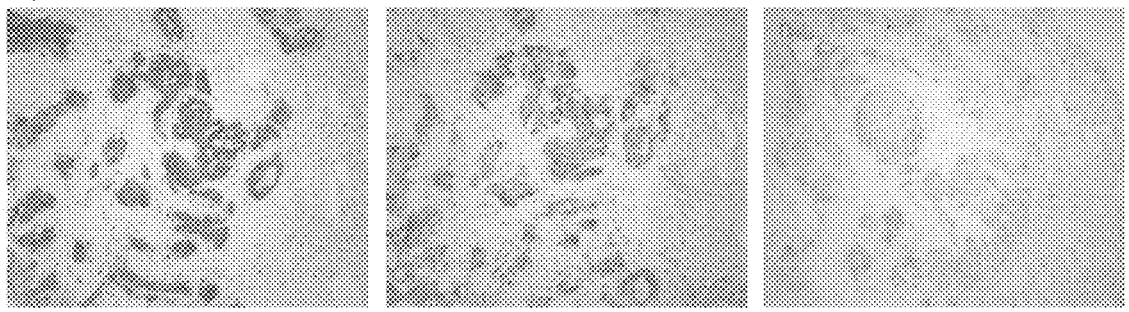
FIG. 4 shows the reactivity of L2A5 antibody, measured by immunohistochemistry in paraffin embedded bladder cancers a) L2A5 (left) staining presents high extension and strong intensity, while the B72.3 (middle) and TKH2 (right) mAbs that bind only to STn, show less sensibility, transduced in poor intensity and reduced extension of specific staining. b) Sensibility of L2A5 compared with available antibodies. L2A5 (left) recognize reduced amount of antigen (arrows), unlike B72.3 (middle) and TKH2 (right) that present different reactivity in the same regions. C) Effect of sialidase treatment of cancer tissues in the antibody reactivity. After treatment with sialidase and incubation with L2A5, the staining granted by L2A5 disappears completely. Left: without sialidase; Right: with sialidase.
Figure 4:
Figure 4:
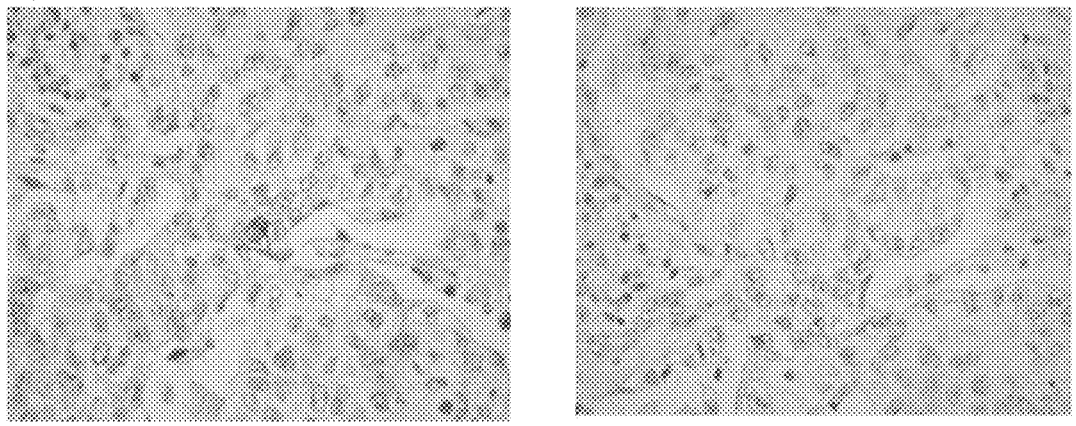

A series of 30 cases with 15 bladder tumours (eight cystectomies and seven metastasis) and 15 colorectal tumours (adenocarcinomas and adenomas) were stained with L2A5 and two anti-STn mAbs. As shown in FIG. 4, all bladder tumours were positive for all the analysed mAbs, regarding metastasis cases. Three of them were positive and three were negative for L2A5, B72.3 and TKH2 mAbs. One case presents a reduced staining with L2A5 and not with the other mAbs. Note for a slight higher sensibility of antigen detection for L2A5. As shown in FIG. 4, while TKH2 and B72.3, show similar reactivity, the L2A5 reveal a higher reactivity in bladder cancer cases. This specificity and sensibility was abrogated after enzymatic treatment of the cancer tissue with sialidase.

Figure 5:
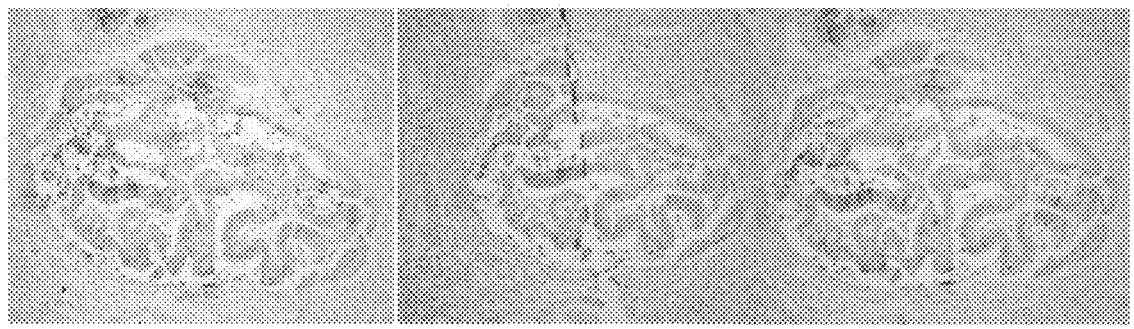
FIG. 5 shows the reactivity of L2A5 antibody, measured by immunohistochemistry in paraffin embedded colorectal cancers. Figure shows the reactivity of L2A5 compared with antibodies against the STn antigen. L2A5 (left) present increased reactivity in terms of extension and intensity when compared with B72.3 (middle) and TKH2 (right) reactivity.

As shown in FIG. 5, all colorectal cancer cases were positive for anti-STn mAbs and for L2A5, but exhibited different patterns in terms of extension and intensity. The L2A5 (left) binding shows similar intensity and extension for most of the pathological tissues (approximately 70%), as compared with B72.3 (middle) or TKH2 (right) staining pattern.

Figure 6:
FIG. 6 shows the reactivity of L2A5 antibody, by immunohistochemistry in paraffin embedded bladder cancers. Figures shows immunohistochemical evidences of high specificity of L2A5 antibody when compared with B72.3 and TKH2 anti-STn antibodies. a)—Tumour specificity of L2A5 in metastatic bladder cancer sample. L2A5 is mainly present in tumour cells (arrows), not existing stain in lymphocytic population, vessels and connective tissues. b)—reactivity of L2A5 (left) and B72.3 (right) antibodies in normal colorectal tissues. L2A5 present faint reactivity with enterocytes (arrow, left) while B72.3 reacts with goblet cells (right).
Figure 6:
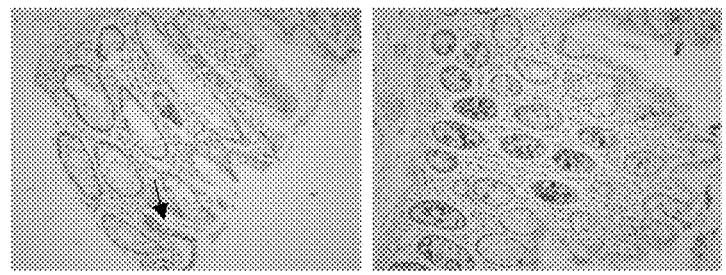
Figure 8:
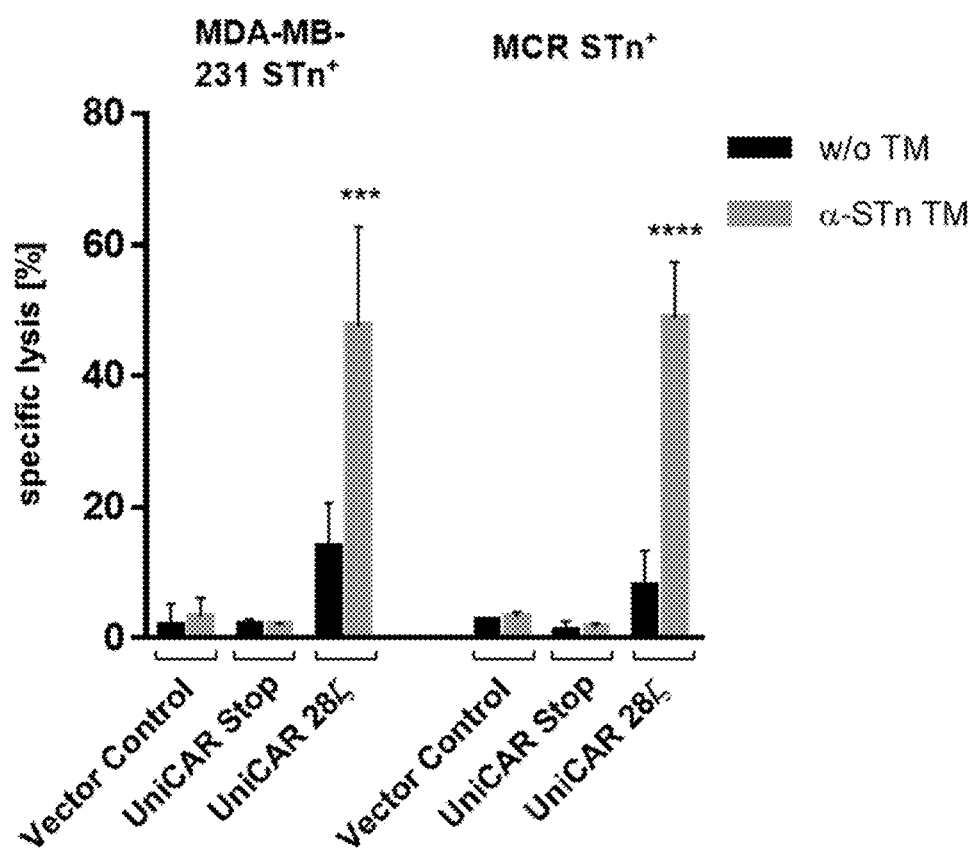
FIG. 8 shows the in vivo anti-tumour capacity of a target module (TM) composed of a moiety containing amino acids coded by the nucleic acids of the L2A5, object of the present invention. The L2A5 derived TM is an antibody fragment and has the same reactivity as the L2A5, i.e. anti-STn TM. Killing of STn-positive cells via UniCAR T cells was target specific and strictly dependent on the presence of TM.
Figure 9:
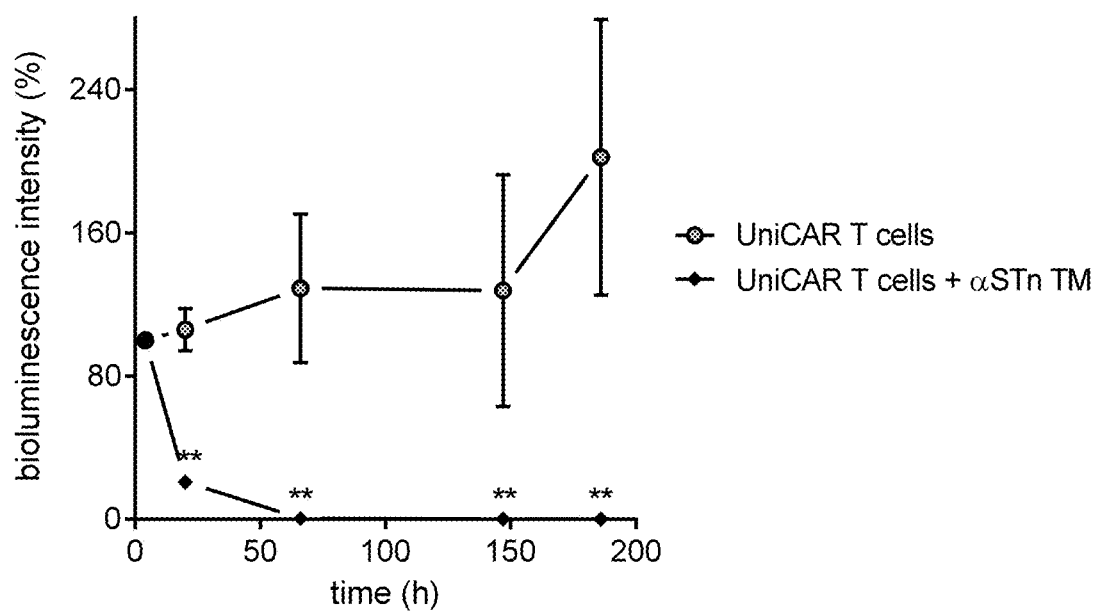
FIG. 9 shows the in vivo anti-tumour capacity of a target module (TM) composed of a moiety containing amino acids coded by the nucleic acids of the L2A5, object of the present invention. The L2A5 derived TM is an antibody fragment and has the same reactivity as the L2A5, i.e. anti-STn TM. The adoptive transfer of the anti-STn TM and UniCAR T cells (Koristka et al 2014) into an animal model expressing STn+ tumours show effective and TM-dependent eradication of STn-positive tumours.

As shown in FIG. 6 a), in metastatic bladder cancer sample the L2A5 is mainly reactive with tumour cells and not lymphocytic population, vessels or connective tissues. In FIG. 6 b), normal colorectal cancer tissues, the L2A5 (left) present unspecific stain in the enterocytes while B72.3 (right) reacts with goblet cells.

In the bladder tumour model, L2A5 staining is exclusive tumoral. L2A5 presents a specific stain in the urothelial tumour cells, including additional spots in invasive and metastasis sites with low density of STn.

In the colorectal samples, L2A5 reacts with cancer tissues, but also with non-pathological tissue. The staining is located essentially in the enterocytes, while the unspecific staining obtained with B72.3 or TKH2 is present in the goblet cells. In colorectal samples, there is no specific location of stain, although L2A5 was able to detect the presence of weak staining in the dysplastic tissue with L2A5.

To examine the carbohydrate-binding specificity in further detail, antibodies were analysed using glycan microarrays comprised of structurally diverse glycan probes printed on a suitable solid surface. The results confirmed the specificity with selective recognition of the STn, but binding was also observed to:

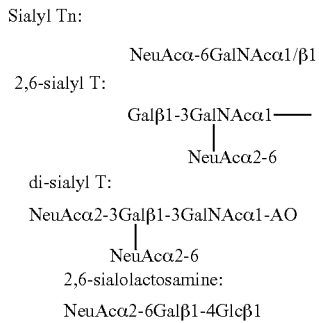

and virtual absence of binding to other antigen sequences that were present in the microarray. The sequences bound are summarized in FIG. 7.

To determine the amino acid sequence of the CDRs (SEQ ID Nos. 6, 8, 10, 12, 14, 16) and FR (SEQ ID Nos. 5, 7, 9, 11, 13, 15) variable regions of the L2A5 mAb light and heavy chains a method described in example IX was used.

EXAMPLES

The following examples are provided merely as illustrative of various aspects of the present disclosure and shall not be construed to limit the disclosure in any way. They relate to the antibody characterization, selection and production.

Example I

Antibody Production—Immunizations

Exemplary methods of producing antibodies are provided, but any other standard method can be used.

Monoclonal antibody (mAb) production was performed according to the hybridoma technology. Female Balb/c mice aged 6 weeks (Harlan, UK) were immunized intraperitoneally with 10 μg of ovine submaxillary mucin (OSM) emulsified 1:1 (V/V) with complete Freund's adjuvant (Sigma-Aldrich) followed by 2 additional injections of OSM emulsified with incomplete Freund's adjuvant (Sigma Aldrich) with intervals of 21 days. Blood samples were collected from the mice cheek and collected serum was screened for STn binding specificity by ELISA. If the serum showed the desired and specific immune response, a final boost injection to the corresponding mice would be performed three days before killing and harvesting the spleen.

Example II

ELISA

Mouse serum titrations and screening of hybridoma supernatants were determined by ELISA against bovine submaxillary mucin (BSM), a STn-expressing protein. The wells of a 96-well plate were coated with 50 μl of BSM (3 μg/ml) dissolved in Phosphate Buffered Saline (PBS) and incubated overnight at 4° C. To assess the specific binding of screened hybridoma supernatants to sialylated structures, 50 μl of sialidase, from *Clostridium perfringens* (Roche) at 25 mU/ml diluted in sialidase buffer (10 mM Na$_2$HPO$_4$, pH=6.0) was added to a subset of wells and incubated for 90 min at 37° C. After sialidase treatment, the plates were washed three times with PBS containing 0.05% Tween 20 (PBS-T) followed by blocking with 5% skim milk powder, for 60 min. After PBS-T washes, diluted mouse sera or hybridoma supernatants were added to the wells and incubated for 90 min. Plates were washed four times with PBS-T, followed by incubation with horseradish peroxidase (HRP)-conjugated goat anti-mouse Ig (1:1000) (BD Pharmingen) for 60 min. After three additional washing steps, 50 µl of tetramethylbenzidine (Thermofisher Scientific) substrate was added to each well, plates were incubated in the dark and the reaction was stopped by adding 50 µl of 1M HCl. The Optical Density was measured at 450 nm on a microplate reader. The mouse producing the highest titre of antibodies of interest was selected for fusion. To screen the antibody production of hybridoma cells, the same procedure was implemented.

Example III

Flow Cytometry Preparation and Analysis

Binding of the antibodies or hybridoma supernatants were determined by flow cytometry using human bladder and breast cell lines stably expressing STn and non-STn expressing parental cells. Approximately $3 \times 10^5$ cells were harvested per condition and resuspended in PBS buffer. To assess the specific binding of screened hybridoma supernatants and antibodies to sialylated structures, samples were treated with sialidase at 100 mU/ml, for 90 min at 37° C. After sialidase treatment, cells were washed and incubated for 30 min at 4° C. with anti-STn mAbs B72.3, 3F1, TKH2 and hybridoma supernatants. Subsequent washing steps were performed, and primary antibodies were detected with FITC conjugated anti-mouse Ig (Dako; dilution 1:10) for 15 min in the dark. After washing, data from each sample was acquired using a Flow Cytometer for each sample.

Example IV

Antibody Production—Hybridoma Technology

Splenocytes from the immunized mouse were mixed with Sp2/0 myeloma (ATCC, USA) cells at a ratio of 3:1 and fused in the presence of polyethylene glycol/dimethylsulphoxide using a standard protocol. Cells were then plated into 96-well flat bottom micro plates (Orange Scientific) and maintained in RPMI medium supplemented with HAT ($1 \times 10^{-4}$ M Hypoxanthine, $4 \times 10^{-7}$ M Aminopterin, $1.6 \times 10^{-5}$ M Thymidine, Sigma-Aldrich), 10% FBS, 2 mM L-glutamine, 0.2 mg/ml Gentamycin (Sigma-Aldrich), 1 mM sodium pyruvate (Gibco), 1% (v/v) MEM non-essential amino acids (Gibco) and incubated at 37° C. for 7-12 days. Hybridoma cells producing antibodies reactive to BSM were expanded and screened by indirect ELISA and cloned by the limited dilution method at least three times to obtain stable single clone cell lines. Selected hybridomas were cultured in the selection medium without HAT supplementation at 37° C. One hybridoma L2A5 specific to the sialylated structures, particularly the STn, was selected and cloned by limiting dilution four times.

Example V

Immunohistochemistry Analysis of STn Expression

A series of 30 cases with 15 colorectal tumours (adenocarcinomas and adenomas) and 15 bladder tumours (eight cystectomies and seven metastasis) were obtained, according to the local committee of ethics. In addition, five cases of tumour-adjacent normal colorectal tissue were included. Formalin-fixed, paraffin embedded (FFPE) tissues were screened for STn by immunohistochemistry (IHC) using the biotin/streptavidin system. Briefly, FFPE tissue sections were deparaffinised with xylene, rehydrated with a graded series of alcohol washes and subjected to heat-induced antigen retrieval using citrate buffer pH 6.0 (Vector, Burlingame, USA) for 15 min in the microwave, after pre-heating of the solution at maximum power rating for 5 minutes. Sections were incubated with 0.3% hydrogen peroxide (Merck KGaA, Darmstadt, Germany) for 25 min, blocked with UV Block® (Thermo Scientific, Fremont, USA) and incubated overnight at 4° C. in a wet chamber with anti-STn mAbs B72.3, TKH2 (Kjeldsen et al., 1988) and L2A5. After washing with PBS-Tween, secondary antibody was added to tissue sections, before incubation with streptavidin. STn was visualized by incubation with 3,3'-diaminobenzidine (ImmPACT™ DAB) (Vector, Burlingame, USA) for 4 min. Finally, nucleus was counterstained with hematoxylin for 1 min. STn expression was assessed using the anti-STn mAbs B72.3, TKH2 and L2A5 hybridoma culture supernatant, diluted 1:5; 1:5 and 1:3 in 5% BSA in PBS, respectively. Positive and negative control sections were tested in parallel. The negative control sections were performed devoid of primary antibody. $STn^+$ tumour tissues were used as positive controls. Tumours were classified as positive when immunoreactivity of anti-STn TKH2 antibody was observed by microscopic presence of brown chromogenic product in tumour cells. STn expression and L2A5 staining were assessed double-blindly by two independent observers and validated by an experienced pathologist. Whenever there was a disagreement, the slides were reviewed, and consensus was reached. In order to evaluate the antibody specificity, sialidase treatment was performed after the incubation with hydrogen peroxide, in which sialic acids are removed from the STn antigen, thereby impairing recognition by the antibody. Therefore, positive staining after this enzymatic treatment (4 h at 37° C.; 0.2 U/mL) was considered as unspecific.

Example VI

Western Blot (WB)

Membrane proteins were isolated from cell lines using Membrane Protein Extraction Kits, according to the manufacturer's instructions. The amount of protein obtained was estimated using Protein Assay Kits, following manufacturer's recommendations. Membrane protein extracts (50 µg) or purified proteins containing STn (1 µg)—BSM and MUC1 STn-IgG—were denatured and loaded onto 8% gradient acrylamide gel, submitted to SDS-PAGE electrophoresis under reducing conditions and electrophoretically transferred onto polyvinylidene difluoride (PVDF) membranes (Amersham Hybond P 0.2 µm PVDF, GE Healthcare Life Sciences) in accordance with standard procedures. Membranes were blocked with 10% skim milk powder in TBS Tween 0.1% (TBS-T) for 1 h followed by incubation with primary antibodies anti-STn B72.3, 3F1 or L2A5 supernatant diluted in TBS-T overnight at 4° C. After washing with TBS-T, labelled proteins were revealed using HRP conjugated goat Anti-Mouse Ig diluted 1:2500 in TBS-T for 1 h. After washing, labelled proteins were revealed by Lumi-Light Western Blotting Substrate (Roche), and then exposed to an X-ray film.

Example VII

Isolation of mRNA and cDNA Synthesis

Between $1\times10^6$ and $5\times10^6$ hybridoma cells were used for RNA isolation. Cells were centrifuged for 5 min at 300×g and the supernatant was discarded. Cell pellet was washed with PBS and total RNA was isolated using GenElute™ Mammalian Total RNA Miniprep Kit (Sigma-Aldrich), according to manufacturer's instructions. Total RNA extracted was quantified using Nanodrop and up to 2 μg was used for reverse transcription as described in High-Capacity cDNA Transcription Kit (Applied Biosystems). cDNA synthesis was performed using the following thermal cycling conditions: 25° C. for 10 min, followed by 37° C. for 120 min and 85° C. for 5 sec. The reactions were finally held and cooled at 4° C.

Example VIII

Antibody Sequencing—scFv Fragments

Variable heavy ($V_a$) and light-chain ($V_L$) domains of L2 A5 MAb were amplified from the cDNA using the primer pair $V_H$ Forward (TTTTTGGATCCSARTN-MAGCTGSAGSAGTCWGG (SEQ ID No. 22))/$V_H$ Reverse (ATTGGGACTAGTTTCTGCGACAGCTGGATT (SEQ ID No. 23)) and $V_L$ Forward (TTTTTGAATTCT-GAYATTGTGMTSACMCARWCTMCA (SEQ ID No 24))/$V_L$ Reverse (TTTTTGGGCCCGGATA-CAGTTGGTGCAGCATC (SEQ ID No. 25)). All PCRs were performed with the Advantage HF 2 PCR Kit (Clontech). The following thermal cycling conditions were used: initial melt at 94° C. for 3 min, followed by 95° C. for 45 sec., 70° C. for I min, and 68° C. for 2 min. The reactions were then held at 68° C. for 5 min and cooled to 4° C. Purified PCR products were further cloned into the pGEM-Teasy (Promega) cloning vector, according to manufacturer's protocols. Plasmids were isolated using the QIAGEN plasmid plus midi kit (QIAGEN), according to the manufacturer protocol, Sequencing was performed by Seqlab (Gottingen, Germany) using the T7 promoter primer for pGEM-Teary vector.

These compositions can be produced in consistent quality for clinical and diagnostic applications.

Example IX

Antibody Domains

The Variable heavy (VH) and light-chain (VL) nucleotide sequences coding for the amino acid sequences of FR and CDRs domains of L2A5 mAb were determined searching the IMGT V domain delineation system (international ImMunoGeneTics database; http://imgt.cines.fr) using the sequence analysis tool IgBLAST.

Example X

Cloning of Nucleic Acids into a Target Module

Anti-STn target module (TM) was performed as described (Cartellieri et al 2016), but replacing the CDR regions by the LA25 nucleic acid sequences. T cell mediated tumour killing was measured using standard chromium release assays. MDA-MB-231 and MCR STn+ cell lines were incubated with T cells engrafted with either the vector control (vector backbone encoding only the EGFP marker protein), Uni-CAR Stop construct (lacking intracellular signaling domains) or α-E5B9 signaling construct (UniCAR 28/ζ) (Mitwasi 2017). Both cell lines were cultivated with the respective genetically engineered T cells in the presence or absence of 80 nM of anti-STn TM (a-STn TM) for 24 h in an effector-to-target (E:T) ratio of 5:1.

Example XI

In Vivo Anti-tumour Activity

MDA-MB-231 STn cells were transduced to express firefly luciferase (Luc) resulting in MDA-MB-231 STn-Luc cells. Anti-STn target module (TM) was performed as described (Cartellieri et al 2016), but replacing the CDR regions by the LA25 nucleic acid sequences. Per mouse, 1.5×06 tumour cells were mixed with 1×106 UniCAR 28/ζ T cells and 10 μg of anti-STn TM. MDA-MB-231 STn-Luc cells (1.5×106) alone or mixed with 1×106 UniCAR 28/ζ T cells without TM were used as untreated controls. Respective mixture was injected subcutaneously into female NMRI-Foxn1nu/Foxn1nu mice resulting in three groups of animals each consisting of five mice. Luminescence imaging of anesthetized mice was performed 10 min after i.p. injection of 200 μL of D-luciferin potassium salt (15 mg/mL) starting at day 0 and followed at day 1, 3, 6 and 8.

The present invention will provide new products both in the antibodies market and cancer research/development field.

This invention provides compositions to produce an antibody or functional antibody fragments or probes thereof directed against a group of antigens identified in cancer.

Table 1 shows an example of the nucleotide sequence of the variable heavy (VH) and variable light (VL) chains of the clone L2A5 identified as SEQ ID Nos. 1 and 2, respectively and the encoded amino acid sequence of the variable heavy (VH) and variable light (VL) chains identified as SEQ ID Nos. 3 and 4 respectively.

TABLE 1

Example of nucleotide sequence and the encoded amino acid sequence of the variable light (VL) and variable heavy (VH) chains of the clone L2A5.

| SEQ ID No. | Chain (mu) |
|---|---|
| 1 | Nucleotide sequence of the variable heavy (VH) chain |
| 2 | Nucleotide sequence of the variable light (VL) chain |
| 3 | Amino acid sequence of VH chain |
| 4 | Amino acid sequence of VL chain |

Table 2 shows the encoded amino acid sequence of the six framework (FR) and six complementarity determining regions (CDR) (H-CDR1, H-CDR2 and H-CDR3, L-CDR1, L-CDR2, LCDR3) for the clone L2A5 and are identified as the nucleotide sequence of SEQ ID NO: 5 to 16.

TABLE 2

Encoded amino acid sequence of the three framework (FR) and three complementarity determining regions (CDR) (H-CDR1, H-CDR2 and H-CDR3, L-CDR1, L-CDR2, LCDR3) for the clone L2A5.

| SEQ ID No. | Region |
|---|---|
| 5 | L-FR1 Amino acid sequence |
| 6 | L-CDR1 Amino acid sequence |
| 7 | L-FR2 Amino acid sequence |
| 8 | L CDR2 Amino acid sequence |
| 9 | L-FR3 Amino acid sequence |
| 10 | L-CDR3 Amino acid sequence |
| 11 | H-FR1 Amino acid sequence |
| 12 | H-CDR1 Amino acid sequence |
| 13 | H-FR2 Amino acid sequence |
| 14 | H-CDR2 Amino acid sequence |
| 15 | H-FR3 Amino acid sequence |
| 16 | H-CD3 Amino acid sequence |

The invention claimed is:

1. An antibody comprising a combination of a light chain variable region (VL) and a heavy chain variable region (VH), wherein:
the VL comprises complementarity determining regions (CDRs) L-CDR1, L-CDR2, and L-CDR3 as set forth in SEQ ID NOs. 6, 8, and 10, respectively; and,
the VH comprising CDRs H-CDR1, H-CDR2 and H-CDR3 as set forth in SEQ ID NOs. 12, 14 and 16, respectively.

2. The antibody of claim 1 wherein the VL comprises SEQ ID NOs. 5, 7, and 9; and the VH comprises SEQ ID NOs. 11, 13 and 15.

3. The antibody of claim 1 wherein the VL comprises SEQ ID No. 4 and the VH comprises SEQ ID No. 3.

4. The antibody of claim 1 that binds STn and a group of glycans terminated by alpha 2,6-linked sialic acids.

5. The antibody of claim 2 wherein the glycans terminated by alpha 2,6-linked sialic acids comprise STn, 2,6-sialyl T, di-sialyl T, or 2,6-sialolactosamine.

6. The antibody of claim 1 that is subject to glycan changes at glycosylation sites.

7. The antibody of claim 1 that is a monoclonal antibody, chimeric antibody, or a humanized antibody.

8. The antibody of claim 1 that is a functional antibody fragment or probe thereof that binds STn and a group of glycans terminated by alpha 2,6-linked sialic acids.

9. A composition comprising the antibody of claim 1 and a pharmaceutically acceptable carrier.

10. A composition comprising the monoclonal antibody of claim 7 and a pharmaceutically acceptable carrier.

11. A method comprising contacting a cell with an antibody of claim 1, or a composition comprising the same; and optionally detecting the antibody.

12. A method comprising contacting a cell with an antibody of claim 7, or a composition comprising the same; and optionally detecting the antibody.

13. A method comprising administering an antibody of claim 1 to a patient having a disease.

14. The method of claim 13 wherein the disease is cancer.

15. A method comprising administering an antibody of claim 7 to a patient having a disease.

16. The method of claim 15 wherein the disease is cancer.

17. A polynucleotide encoding the antibody of claim 1.

18. The polynucleotide of claim 17 comprising SEQ ID NO. 1 and/or SEQ ID NO. 2; SEQ ID NOs. 17, GACACATCC, and SEQ ID NO. 19; or, SEQ ID NOs. 19, 20 and 21.

19. An expression vector comprising the polynucleotide of claim 17.

20. A host cell comprising an expression vector of claim 19.

21. A method of producing an antibody using a host cell of claim 20.

* * * * *

UNITED STATES PATENT AND TRADEMARK OFFICE
CERTIFICATE OF CORRECTION

PATENT NO. : 11,353,460 B2
APPLICATION NO. : 16/964900
DATED : June 7, 2022
INVENTOR(S) : Paula Alexandra Quintela Videira et al.

It is certified that error appears in the above-identified patent and that said Letters Patent is hereby corrected as shown below:

In the Specification

Column 25, SEQ ID No. 17, "TGAAGTGTAAGTTAC" should read -- "TCAAGTGTAAGTTAC" --

Signed and Sealed this
Third Day of January, 2023

Katherine Kelly Vidal
*Director of the United States Patent and Trademark Office*